United States Patent [19]

Herzig et al.

[11] Patent Number: 5,118,772

[45] Date of Patent: Jun. 2, 1992

[54] ALKENYLOXY-FUNCTIONAL ORGANOSILICON COMPOUNDS, THEIR PREPARATION AND USE

[75] Inventors: Christian Herzig, Taching; Doris Gilch, Eggenfelden, both of Fed. Rep. of Germany

[73] Assignee: Wacker-Chemie GmbH, Munich, Fed. Rep. of Germany

[21] Appl. No.: 718,688

[22] Filed: Jun. 21, 1991

Related U.S. Application Data

[62] Division of Ser. No. 519,370, May 4, 1990, Pat. No. 5,057,549.

[30] Foreign Application Priority Data

Apr. 5, 1989 [DE] Fed. Rep. of Germany ....... 3914896

[51] Int. Cl.$^5$ .................................... C08F 130/08
[52] U.S. Cl. .................................... 526/279; 528/15; 528/31; 528/32; 556/427; 556/438; 556/439; 556/444; 556/445
[58] Field of Search ............... 556/427, 438, 439, 444, 556/445; 526/279; 528/15, 31, 32

[56] References Cited

U.S. PATENT DOCUMENTS

| | | | |
|---|---|---|---|
| 4,150,048 | 4/1979 | Schilling, Jr. et al. | 556/444 |
| 4,742,136 | 5/1988 | Uchida | 526/279 |
| 4,929,647 | 5/1990 | Burger et al. | 528/32 X |

*Primary Examiner*—Joseph L. Schofer
*Assistant Examiner*—M. Nagumo

[57] ABSTRACT

Novel, alkenyloxy-functional organosilicon compounds are described which contain at least one Si-bonded Y radical per molecule having the formula $$-(CH_2)_2-R^2-(A-R^3)_z-O-CH=CH-CH_2-R^4 \qquad (I).$$

in which

A represents —O—, —S— or

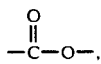

$R^2$ represents a linear or branched alkylene radical having from 1 to 7 carbon atom(s) per radical or a cycloalkylene radical having from 5 to 7 carbon atoms per radical, $R^3$ represents a linear or branched alkylene radical having from 2 to 4 carbon atoms per radical, which may be substituted by a hydroxyl group, methoxy group, ethoxy group or trimethylsiloxy group, $R^4$ represents a hydrogen atom or an alkyl radical having from 1 to 4 carbon atoms(s) per radical, and z is 0, 1 or 2.

The alkenyloxy-functional organosilicon compounds are preferably silanes or organopolysiloxanes.

The alkenyloxy-functional organopolysiloxanes can be crosslinked, for example, with ultraviolet light. These organopolysiloxanes can also be used for preparing coatings.

8 Claims, No Drawings

ALKENYLOXY-FUNCTIONAL ORGANOSILICON COMPOUNDS, THEIR PREPARATION AND USE

This is a division of application Ser. No. 07/519,370, filed May 4, 1990, now U.S. Pat. No. 5,057,549.

The present invention relates to novel, alkenyloxy-functional organosilicon compounds.

BACKGROUND OF THE INVENTION

U.S. Pat. No. 4,617,238 to Crivello et al discloses organopolysiloxanes containing at least one Si-bonded vinyloxy-functional group per molecule of the formula $$H_2C=CH-O-G-$$

where G represents an alkylene radical or an alkylene radical which is interrupted by at least one divalent heteroatom or a combination of heteroatoms. U.S. Pat. No. 4,617,238 describes light-crosslinkable compositions which contain the abovementioned organopolysiloxanes, and also onium salts which catalyze the cationic polymerization of these organopolysiloxanes.

Therefore, it is an object of the present invention to provide organosilicon compounds, in particular silanes and organopolysiloxanes, which contain at least one Si-bonded Y radical of formula (I) per molecule. Another object of the present invention is to provide organosilicon compounds having at least one Si-bonded Y radical of formula (I) which can be prepared from readily available starting materials. Still another object of the present invention is to provide organopolysiloxanes having at least one Si-bonded Y radical of formula (I) per molecule which crosslink rapidly when exposed to light, especially ultraviolet light, during cationic polymerization.

SUMMARY OF THE INVENTION

The foregoing objects and others which will become apparent from the following description are accomplished in accordance with this invention, generally speaking, by providing organosilicon compounds which contain at least one Si-bonded Y radical per molecule having the formula $$-(CH_2)_2-R^2-(A-R^3)_z-O-CH=CH-CH_2-R^4 \quad (I).$$

in which
A represents $-O-$, $-S-$ or

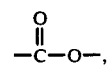

$R^2$ represents a linear or branched alkylene radical having from 1 to 7 carbon atom(s) per radical or a cycloalkylene radical having from 5 to 7 carbon atoms per radical, $R^3$ represents a linear or branched alkylene radical having from 2 to 4 carbon atoms per radical, which may be substituted by a hydroxyl group, methoxy group, ethoxy group or trimethylsiloxy group, $R^4$ represents a hydrogen atom or an alkyl radical having from 1 to 4 carbon atoms(s) per radical, and z is 0, 1 or 2.

The organosilicon compounds according to this invention are preferably silanes or organopolysiloxanes.

DESCRIPTION OF THE INVENTION

The organosilicon compounds are preferably those of the general formula $$R_a(R^1O)_bY_cSiO_{\frac{4-(a+b+c)}{2}}$$

in which a is 0, 1, 2 or 3, with an average of from 0.0 to 3.0, b is 0, 1, 2 or 3, with an average of from 0.0 to 3.0 and c is 0 or 1, with an average of from 0.01 to 1.0 and the sum of a+b+c is $\leq 4$, with an average of from 1.0 to 4.0, R may be the same or different, and represents a monovalent substituted or unsubstituted hydrocarbon radical having from 1 to 18 carbon atom(s) per radical, $R^1$ may be the same or different, and represents a monovalent hydrocarbon radical having from 1 to 8 carbon atom(s) per radical which may be interrupted by an ether oxygen atom, and Y is a radical of the formula $$-(CH_2)_2-R^2-(A-R^3)_z-O-CH=CH-CH_2-R^4 \quad (I).$$

in which A represents $-O-$, $-S-$ or

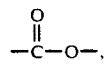

$R^2$ represents a linear or branched alkylene radical having from 1 to 7 carbon atom(s) per radical or a cycloalkylene radical having from 5 to 7 carbon atoms per radical, $R^3$ represents a linear or branched alkylene radical having from 2 to 4 carbon atoms per radical, which may be substituted by a hydroxyl group, methoxy group, ethoxy group or trimethylsiloxy group, $R^4$ represents a hydrogen atom or an alkyl radical having from 1 to 4 carbon atoms(s) per radical, and z is 0, 1 or 2. Preferably these organosilicon compounds have a molecular weight of preferably from 188 to 300,000 g/mole, and more preferably a molecular weight of from 232 to 30,000 g/mole.

Preferred organosilicon compounds having at least one Si-bonded Y radical per molecule are silanes of the formula $$R_dYSi(OR^1)_{3-d}.$$

having a viscosity of from 1.5 to 100 mm$^2$.s$^{-1}$ at 25° C., or organopolysiloxanes of the formula $$Y_cR_{3-c}SiO(SiR_2O)_n(SiRYO)_mSiR_{3-c}Y_c$$

having a viscosity of at least 4 mm$^2$.s$^{-1}$ at 25° C., and more preferably from 4 to 20,000 mm$^2$.s$^{-1}$ at 25° C., where R, $R^1$, Y and c are the same as above, d is 0, 1 or 2, n is 0 or an integer of from 1 to 1000 and m is 0 or an integer of from 1 to 500.

Examples of radicals represented by R are alkyl radicals, such as the methyl, ethyl, n-propyl, iso-propyl, 1-n-butyl, 2-n-butyl, iso-butyl, tert-butyl, n-pentyl, iso-pentyl, neo-pentyl or tert-pentyl radicals, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical, octadecyl radicals, such as the n-octadecyl radical; alkenyl radicals, such as the vinyl and the allyl radicals; cycloalkyl radicals, such as the cyclopentyl, cyclohexyl, or cycloheptyl radicals and methylcyclohexyl radicals; aryl radicals, such as the phenyl, naphthyl, anthryl and phenanthryl radicals; alkaryl radicals, such as o-, m-, p-tolyl radicals, xylyl radicals and ethylphenyl radicals; and aralkyl radicals, such as the benzyl radical, the $\alpha$- and the $\beta$-phenylethyl radicals, with the methyl radical being the preferred radical.

Examples of substituted radicals represented by R are cyanoalkyl radicals, such as the $\beta$-cyanoethyl radical, and halogenated hydrocarbon radicals, for example, the halogenoalkyl radicals, such as the 3,3,3-trifluoro-n-propyl radical, the 2,2,2,2',2',2'-hexafluoroisopropyl radical, the hepta fluoroisopropyl radical and halogenoaryl radicals, such as the o-, m-, and p-chlorophenyl radicals.

Examples of radicals represented by $R^1$ are alkyl radicals, such as the methyl, ethyl, n-propyl, iso-propyl, 1-n-butyl, 2-n-butyl, iso-butyl and tert-butyl radicals. Preferably, the $R^1$ radicals are the methyl and ethyl radicals. Examples of a hydrocarbon radical represented by $R^1$ which is interrupted by at least one ether oxygen atom are the methoxyethyl radical and the ethoxyethyl radical. Examples of alkylene radicals represented by $R^2$ are those of the formula

—CH$_2$—

—(CH$_2$)$_2$—

—CH(CH$_3$)— and

—(CH$_2$)$_3$—.

Examples of cycloalkylene radicals represented by $R^2$ are the cyclohexylene radical and the methyl cyclohexylene radical.

Preferably, the $R^2$ radical has the formula

—CH$_2$—.

A is preferably oxygen (—O—).

Examples of radicals represented by $R^3$ are those of the formula

—(CH$_2$)$_2$—

—(CH$_2$)$_3$—

—CH$_2$CH(CH$_3$)CH$_2$—

—CH$_2$CH(OH)CH$_2$—

—CH$_2$CH(OCH$_3$)CH$_2$—

—CH$_2$CH(OC$_2$H$_5$)CH$_2$— and

—CH$_2$CH[OSi(CH$_3$)$_3$]CH$_2$—.

Examples of radicals represented by $R^4$ are alkyl radicals, such as the methyl, ethyl, n-propyl, iso-propyl, 1-n-butyl, 2-n-butyl, iso-butyl and tert-butyl radicals. The $R^4$ radical is preferably a hydrogen atom or a methyl radical.

Examples of radicals represented by Y are those of the formula

—(CH$_2$)$_3$—O—CH=CH—CH$_3$

—(CH$_2$)$_3$—O—CH$_2$—CH$_2$—O—CH=CH—CH$_3$

—(CH$_2$)$_3$—O—CH=CH—CH$_2$—CH$_3$ and

—(CH$_2$)$_3$—O—CH$_2$—CH—CH$_2$—O—CH=CH—CH$_3$,
                      |
                      OZ where Z is a hydrogen atom or a radical of the formula —CH$_3$, —C$_2$H$_5$ or —Si(CH$_3$)$_3$.

Examples of preferred Y radicals are those of the formula

—(CH$_2$)$_3$—O—CH=CH—CH$_3$

—(CH$_2$)$_3$—O—CH$_2$—CH$_2$—O—CH=CH—CH$_3$
and

—(CH$_2$)$_3$—O—CH=CH—CH$_2$—CH$_3$, and more preferably the Y radical has the formula

—(CH$_2$)$_3$—O—CH=CH—CH$_3$.

The invention furthermore relates to a process for the preparation of organosilicon compounds having at least one Si-bonded Y radical of formula (I) per molecule, which comprises reacting in a 1st step an organic compound (1) of the formula H$_2$C=CH—R$^2$—(A—R$^3$)$_z$—O—CH$_2$—CH=CH—R$^4$ in which $R^2$, $R^3$, $R^4$, A and z are the same as above, with an organosilicon compound (2) having at least one Si-bonded hydrogen atom in the presence of a catalyst (3) which promotes the addition of Si-bonded hydrogen to the aliphatic double bond. An organosilicon compound having at least one Si-bonded $Y^1$ radical of the formula —(CH$_2$)$_2$—R$^2$—(A—R$^3$)$_z$—O—CH$_2$—CH=CH—R$^4$   (II), in which $R^2$, $R^3$, $R^4$, A and z are the same as above, is obtained, and then in a 2nd step shifting the double bond in the $Y^1$ radical to the carbon atom adjacent to the ether oxygen atom by heating the organosilicon compound having at least one Si-bonded $Y^1$ radical, obtained in the 1st step, in the presence of a catalyst (4) which promotes this kind of rearrangement of the double bond. Any organosilicon compound having at least one Si-bonded Y radical of the formula —(CH$_2$)$_2$—R$^2$—(A—R$^3$)$_z$—O—CH=CH—CH$_2$-R$^4$   (I), in which $R^2$, $R^3$, $R^4$, A and z are the same as above, is obtained.

In order to prepare the organosilicon compounds of this invention, an organosilicon compound (2) having at least one Si-bonded hydrogen atom is used which is preferably a silane (2a) of the formula R$_d$HSiX$_{3-d}$, in which R and d are the same as above, X may be the same or different, and is a halogen atom, preferably a chlorine atom, or a radical of the formula —OR$^1$, where $R^1$ is the same as above, or is an organopolysiloxane (2b) of the formula $$H_cR_{3-c}SiO(SiR_2O)_o(SiRHO)_pSiR_{3-c}H_c.$$

in which R and c are the same as above, o represents 0 or an integer of from 1 to 1000 and p represents 0 or an integer of from 1 to 500, with the proviso that at least one Si-bonded hydrogen atom is present per molecule.

Organopolysiloxanes having at least one Si-bonded Y radical of formula (I) per molecule can be prepared from silanes in a modified process in which in a 1st step an organic compound (1) of the formula $$H_2C=CH-R^2-(A-R^3)_z-O-CH_2-CH=CH-R^4$$

in which $R^2$, $R^3$, $R^4$, A and z are the same as above, is reacted with a silane (2a) having an Si-bonded hydrogen atom of the formula $$R_dHSiX_{3-d}.$$

in which R, X and d are the same as above, in the presence of a catalyst (3) which promotes the addition of Si-bonded hydrogen to the aliphatic double bond, to form a silane having an Si-bonded $Y^1$ radical of the formula $$-(CH_2)_2-R^2-(A-R^3)_z-O-CH_2-CH=CH-R^4 \quad (II).$$

in which $R^2$, $R^3$, $R^4$, A and z are the same as above, from which hydrolysis with chloro- or alkoxysilanes and/or condensation with condensable organopolysiloxanes in a manner known per se subsequently produces an organopolysiloxane having at least one Si-bonded $Y^1$ radical of the formula $$-(CH_2)_2-R^2-(A-R^3)_z-O-CH_2-CH=CH-R^4 \quad (II).$$

in which $R^2$, $R^3$, $R^4$, A and z are the same as above, and in a 2nd step the double bond in the $Y^1$ radical of the organopolysiloxane is shifted to the carbon atom adjacent to the ether oxygen atom by heating the organopolysiloxane having at least one $Y^1$ radical, obtained in the 1st step, in the presence of a catalyst (4) which promotes this kind of rearrangement of the double bond, and thereafter an organopolysiloxane having at least one Si-bonded Y radical of the formula $$-(CH_2)_2-R^2-(A-R^3)_z-O-CH=CH-CH_2-R^4 \quad (I),$$

in which $R^2$, $R^3$, $R^4$, A and z are the same as above, is obtained.

The organic compounds (1) are preferably used in the addition reaction carried out in the 1st step of the process according to the invention in amounts such that at least 1 mole, preferably at least 1.5 moles, of organic compound (1) is present per gram-atom of Si-bonded hydrogen in the organosilicon compound (2). If $R^4$ in the organic compound (1) is hydrogen, preferably the organic compound (1) is used in an amount such that 4 to 8 moles of organic compound are present per gram-atom of Si-bonded hydrogen in the organosilicon compound (2). This excess of organic compound (1) ensures that the addition does not take place at both terminal aliphatic double bonds but at only one in each case, and thus diaddition is suppressed.

Examples of organic compounds (1) which are used in the addition reaction which occurs in the 1st step of the process according to this invention are those of the formula $$CH_2=CHCH_2OCH_2CH=CH_2 \text{ (diallyl ether)}$$

$$CH_2=CHCH_2OCH_2CH_2OCH_2CH=CH_2$$
[ethylene glycol bis(allyl ether)]

$$CH_2=CHCH_2OCH_2CH=CHCH_3$$
(allyl but-2-enyl ether)

and $$CH_2=CHCH_2OCH_2\underset{OZ}{CH}CH_2OCH_2CH=CH_2$$

where Z represents a hydrogen atom or a radical of the formula $-CH_3$, $-C_2H_5$ or $-Si(CH_3)_3$.

Preferred organic compounds (1) employed in the process of this invention are diallyl ether, ethylene glycol bis(allyl ether) and allyl but-2-enyl ether, and more preferably a diallyl ether is employed.

The organic compounds (1) are readily obtainable, as shown by the following exemplary reactions, which take place under basic conditions and phase transfer catalysis:

$$CH_2=CHCH_2Cl + HOCH_2CH=CHR^4 \longrightarrow$$

$$CH_2=CHCH_2OCH_2CH=CHR^4$$
$$(R^4 = H, -CH_3)$$

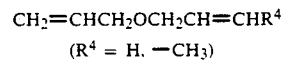

$$(z + 1) CH_2\overset{O}{-\!\!\!-\!\!\!-}CH_2 + HOCH_2CH=CH_2 \longrightarrow$$

(z = 0, 1 or 2)

$$H(OCH_2CH_2)_zOCH_2CH=CH_2$$

$$CH_2=CHCH_2Cl + \downarrow$$

$$CH_2=CHCH_2(OCH_2CH_2)_zOCH_2CH=CH_2$$

$$CH_2=CHCH_2OH +$$

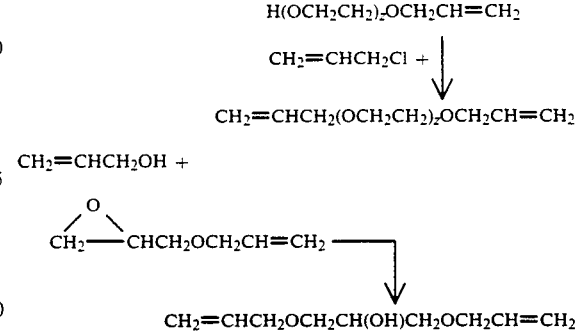

$$CH_2=CHCH_2OCH_2CH(OH)CH_2OCH_2CH=CH_2$$

Processes for their preparation are, for example, described in H. H. Freedman and R. A. Dubois, Tetrahedron Letters No. 38, page 3251 to 3254, 1975; Houben-Weyl, Methoden der organischen Chemie, volume VI/3, page 24 to 32, 1965; and GB-A 913,919.

Catalysts (3) promoting the addition of Si-bonded hydrogen to the aliphatic double bond which are used in the process of this invention may also be the same catalysts which heretofore could have been used to promote the addition of Si-bonded hydrogen to aliphatic double bonds. Catalyst (3) is preferably a metal from the group of platinum metals or a compound or complex from the group of platinum metals. Examples of catalysts of this type are metallic and finely divided platinum, which can be supported on carriers, such as silicon dioxide, aluminum oxide or activated carbon, compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum alcoholate complexes, platinum ether complexes, platinum aldehyde complexes, platinum ketone complexes, including reaction products of $H_2PtCl_6 \cdot 6H_2O$ and cyclohexanone, platinum-vinyl siloxane complexes, such as platinum, 1,3-divinyl-1,1,3,3-tetramethyldisiloxane complexes with or without detectable inorganically-bound halogen, bis(gammapicoline)platinum dichloride, trimethylene dipyridine platinum dichloride, dicyclopentadiene platinum dichloride, dimethylsulfoxide ethylene platinum(II) dichloride and also reaction products of platinum tetrachloride with an olefin and a primary amine or a secondary amine or a primary and a secondary amine according to U.S. Pat. No. 4,292,434 to Lindner et al, such as the reaction product from platinum tetrachloride dissolved in 1-octene with sec-butylamine or ammonium platinum complexes according to EP-B 110,370.

Catalyst (3) is preferably used in an amount of from 0.1 to 10,000 ppm (parts by weight per million parts by weight), and more preferably in an amount of from 10 to 100 ppm, calculated as the elemental metal, from the group of platinum metals and based on the total weight of organic compound (2) having at least one Si-bonded hydrogen atom.

The addition reaction (or hydrosilylation reaction) in the 1st step of the process according to this invention is preferably carried out at atmospheric pressure, i.e., at about 1020 hPa (abs.), but it may also be carried out at higher or lower pressures. Furthermore, the addition reaction is preferably carried out at a temperature of from 40° to 200° C., and more preferably from 70° to 140° C.

The hydrosilylation carried out in the 1st step of the process of this invention produces organosilicon compounds having at least one Si-bonded $Y^1$ radical of the formula $$-(CH_2)_2-R^2-(A-R^3)_z-O-CH_2-CH=CH-R^4 \qquad (II).$$

in which $R^2$, $R^3$, $R^4$, A and z are the same as above. Excess organic compound (1) is removed from the organosilicon compound having at least one Si-bonded $Y^1$ radical by distillation.

The silanes having an Si-bonded $Y^1$ radical of formula (II) which are obtained in the 1st step of the process of this invention can be reacted by mixed hydrolysis with chloro- or alkoxy-silanes and/or by condensation with condensable organopolysiloxanes in a manner known per se to form organopolysiloxanes having at least one Si-bonded $Y^1$ radical of formula (II) per molecule.

Preferably, chloro- or alkoxy-silanes of the formula $R_eSiX_{4-e}$, are used, in which R is the same as above, X is the same or different, and is a chlorine atom or a radical of the formula $-OR^1$, where $R^1$ is the same as above, and e is 0, 1, 2 or 3.

Preferably, condensable organopolysiloxanes of the formula $HOR_2SiO(SiR_2O)_qH$, as used, in which R is the same as above and q is an integer having a value of at least 1, or linear, condensable organopolysiloxanes obtained from cyclic organopolysiloxanes of the formula $(SiR_2O)_r$, in which R is the same as above and r is an integer having a value of from 3 to 10, by condensation and/or equilibration in a manner known per se.

The catalysts (4) used to promote the shift of the double bond in the $Y^1$ radical of formula (II) to the carbon atom adjacent to the ether oxygen in the 2nd step of the process according to this invention may be the same catalysts which have been or could have been used heretofore to promote this kind of rearrangement of the double bond. Examples of catalysts (4) are metallic or finely divided platinum, ruthenium, rhodium and palladium, in which these metals may be supported on carriers such as activated carbon, and compounds or complexes of these elements, which are soluble in the organosilicon compound having at least one Si-bonded radical $Y^1$ of formula (II) or which are fixed to carriers such as activated carbon or polymeric phosphine ligands. Examples of preferred catalysts (4) are those of the formula $RuCl_2(PPh_3)_3$, $RuHCl(PPh_3)_3$, $RuHCl(CO)(PPh_3)_3$, $RuH_2(CO)(PPh_3)_3$ and $RuH_2(PPh_3)_4$.

The catalyst (4) is preferably used in an amount of from 0.1 to 1000 mg, preferably from 1 to 50 mg, calculated each case as the elemental metal, per gram-mole of Si-bonded $Y^1$ radical in the organosilicon compound having at least one Si-bonded $Y^1$ radical of formula (II) which is obtained in the 1st step of the process of this invention.

In order to shift the double bond to the carbon atom adjacent to the ether oxygen atom in the $Y^1$ radical of formula (II), the organosilicon compound having at least one Si-bonded $Y^1$ radical of formula (II) obtained from the 1st step of the process of this invention is mixed with catalyst (4) and the mixture is heated. The reaction is preferably carried out at a temperature of from 80° to 200° C., and more preferably from 100° to 150° C., preferably at atmospheric pressure, i.e., at about 1020 hPa (abs.), and preferably over a period of from 2 to 20 hours and more preferably from 4 to 10 hours. It is preferred that the reaction be conducted in the absence of a solvent.

The organosilicon compound having at least one Si-bonded Y radical of formula (I) which is obtained in the 2nd step of the process of this invention is a mixture of cis-/trans-isomers in respect of the radical Y, the cis-isomer usually predominating. If, for example, Y is a 1-propenyloxypropyl radical, the following mixture of isomers is present:

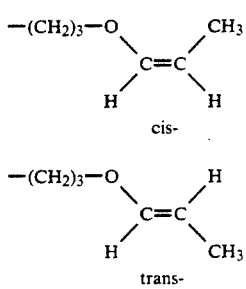

Finally, it is also possible to prepare the organosilicon compounds of this invention having at least one Si-bonded Y radical of formula (I) by reacting an organic compound of the formula

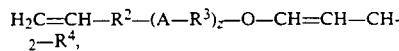

in which $R^2$, $R^3$, $R^4$, A and z are the same as above, with an organosilicon compound (2) having at least one Si-bonded hydrogen atom in the presence of a catalyst (3) which promotes the addition of Si-bonded hydrogen to the aliphatic double bond.

The organopolysiloxanes prepared according to the invention having at least one Si-bonded Y radical of formula (I) are crosslinkable by light-initiated cationic polymerization. Catalysts used for the light-initiated crosslinking may, for example, be the bis(dodecylphenyl)-iodonium salts described in U.S. Pat. No. 4,279,717 to Eckberg et al, such as bis(dodecylphenyl)iodonium hexafluoroantimoate or bis(dodecylphenyl)iodoniumhexafluoroarsenate.

The invention therefore relates to the use of organopolysiloxanes having at least one Si-bonded Y radical per molecule, in which Y is the same as above, in light-crosslinkable compositions based on previously mentioned organopolysiloxanes.

The organopolysiloxanes according to this invention having at least one Si-bonded Y radical of formula (I) are preferably crosslinked by ultraviolet light, preference being given to that having a wavelength in the range of from 200 to 400 nm. The ultraviolet light can be generated, for example, in xenon lamps, low pressure mercury lamps, medium pressure mercury lamps or high pressure mercury lamps. Light-cross-linking is also possible using light with a wavelength of from 400 to 600 nm, i.e., so-called "halogen light". The organopolysiloxanes according to this invention having at least one Si-bonded Y radical of formula (I) can be cross-linked using light in the visible range if commercially available photosensitizers are concomitantly used.

Finally, the invention also relates to the use of the organopolysiloxanes of this invention having at least one Si-bonded Y radical, in which Y is the same as above, in the preparation of light-crosslinkable coatings.

Examples of surfaces to which the coatings of this invention can be applied are those of paper, wood, cork, plastic films, for example, polyethylene films or polypropylene films, ceramic objects, glass, including glass fibers, metals, boards, including those made of asbestos, and of woven and nonwoven cloth made from natural or synthetic organic fibers.

The application of the organopolysiloxanes of this invention having at least one Si-bonded Y radical of formula (I) to the surfaces which are to be coated can be carried out using any suitable and widely known method for producing coatings from liquid substances, for example, by dip coating, brush coating, casting, spray coating, roller coating, printing for example, using an offset gravure roll coater, knife coating or draw bar coating.

EXAMPLE 1

(a) About 28 g of trimethylbenzylammonium chloride (0.1 mole) are added to a solution containing 600 g of NaOH (15 moles) in 600 ml of water. About 290 g of allyl alcohol (5.0 moles) and 425 g of allyl chloride (5.5 moles) are then added to this mixture. The reaction mixture is heated for eight hours at 40° to 60° C. The resulting sodium chloride precipitate is then substantially dissolved in water. The organic phase is separated off and dried using sodium sulfate. Distillation through a short vigreux column at 92° to 94° C. produces 415 g of diallyl ether (85 percent of theory).

(b) About 294 g of diallyl ether, prepared in accordance with (a) above, is initially introduced into a three-necked flask fitted with an internal thermometer and reflux condenser, together with 0.5 ml of a solution of platinum tetrachloride in 1-octene, containing 20 mg of platinum, calculated as the element, and the mixture is heated to reflux temperature. About 118 g of methylhydrogendiethoxysilane is then added dropwise to this mixture over a period of two hours, the temperature of the vapor space remaining between 86° and 91° C. The reaction mixture is allowed to react at this temperature for an additional two hours, then the excess of diallyl ether is distilled off using a short packed column and 125 g of pure (allyloxypropyl)methyldiethoxysilane are obtained by fractional distillation through a vigreux column at 40° to 42° C. and 3 hPa (abs.).

(c) About 200 ppm (based on the total weight of the silane used) of tris(triphenylphosphine)ruthenium(II) dichloride are added to 125 g of the (allyloxypropyl)-methyldiethoxysilane described in (b) above. After heating for four hours at 150° C. (95 percent conversion), (1-propenyloxypropyl)methyldiethoxysilane of the formula

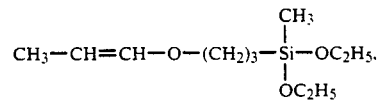

is obtained, which is present as a mixture of cis-/trans-isomers. The following $^1$H—NMR spectrum is obtained from the product:

| $^1$H-NMR spectrum (CDCl$_3$): | |
|---|---|
| trans-isomer: (40 mole-%) | δ = 0.12 ppm (s, 3H, Si—CH$_3$), |
| | 0.65 ppm (m, 2H, Si—CH$_2$—), |
| | 1.22 ppm (t, 6H, Si—O—CH$_2$—C$\underline{H}_3$), |
| | 1.54 ppm (dd, 3H, C$\underline{H}_3$—CH=), |
| | 1.70 ppm (m, 2H, Si—CH$_2$—C$\underline{H}_2$—), |
| | 3.59 ppm (t, 2H, —O—C$\underline{H}_2$—CH$_2$), |
| | 3.76 ppm (q, 4H, Si—O—CH$_2$—), |
| | 4.75 ppm (dq, 1H, CH$_3$—C$\underline{H}$=), |
| | 6.19 ppm (dq, 1H, =CH—O—). |
| cis-isomer: (60 mole-%) | δ = 0.13 ppm (s, 3H, SiCH$_3$), |
| | 0.65 ppm (m, 2H, Si—CH$_2$—), |
| | 1.22 ppm (t, 6H, Si—O—CH$_2$—C$\underline{H}_3$), |
| | 1.58 ppm (dd, 3H, C$\underline{H}_3$—CH=), |
| | 1.70 ppm (m, 2H, Si—CH$_2$—C$\underline{H}_2$—), |
| | 3.69 ppm (t, 2H, —O—C$\underline{H}_2$—CH$_2$—), |
| | 3.77 ppm (q, 4H, Si—O—CH$_2$—), |
| | 4.36 ppm (dq, 1H, CH$_3$—C$\underline{H}$=), |
| | 5.92 ppm (dq, 1H, =CH—O—). |

EXAMPLE 2

(a) About 70 g of the (allyloxypropyl)methyldiethoxysilane described in Example 1(b) above are mixed with 16 g of trimethylethoxysilane and 15 g of water and 2 g of a strongly acid ion exchange medium for six hours at 80° C. The reaction mixture is then filtered and evaporated in vacuo (5 hPa). The residue remaining is 50 g of product, having a viscosity of 15 mm$^2$.s and a ratio of Si-bonded allyloxypropyl radical to Si-bonded methyl radical of 1:2.33, which corresponds to a siloxane of the average composition.

(CH$_3$)$_3$SiO[CH$_3$Si(C$_3$H$_6$OCH$_2$CH=CH$_2$)O]$_4$.5Si(CH$_3$)$_3$.

In order to remove traces of acid, the siloxane obtained in this manner is stirred for 15 hours with MgO in amounts of 5 percent by weight, based on the total weight of siloxane, and then the mixture is filtered.

(b) About 200 ppm (based on the total weight of siloxane) of tris(triphenylphosphine)ruthenium(II) dichloride are added to 50 g of the siloxane described in (a) above. After heating for eight hours at 130° C., a siloxane is obtained having the average composition:

(CH$_3$)$_3$SiO[CH$_3$Si(C$_3$H$_6$OCH=CH—CH$_3$)O]$_4$.5Si(CH$_3$)$_3$ and a ratio of cis-isomer to trans-isomer of 2:1 and with the following $^1$H—NMR spectrum:

| $^1$H-NMR spectrum (CDCl$_3$): | |
|---|---|
| trans-isomer: | δ = 4.77 ppm (dq, 1H, CH$_3$—C$\underline{H}$=), |
| | 6.18 ppm (dq, 1H, =CH—O—). |
| cis-isomer: | δ = 4.35 ppm (dq, 1H, CH$_3$—C$\underline{H}$=), |
| | 5.92 ppm (dq, 1H, =CH—O—). |

EXAMPLE 3

(a) The method described in Example 1(b) above is repeated, except that 101 g of methylhydrogendichlorosilane are used instead of 118 g of methylhydrogendiethoxysilane. Fractional distillation at 80° to 85° C. and 7 hPa (abs.) is used to produce (allyloxypropyl)methyldichlorosilane in 70 percent yield.

(b) About 520 g of a mixture of cyclic dimethylpolysiloxanes having 3 to 7 siloxane units per molecule are stirred for two days with 62.4 g of KOH at 120° C., in which the water formed during the reaction is removed. The linear potassium siloxanolate thus obtained is diluted with 300 g of toluene and cooled to +10° C. To this solution are then added dropwise, so that the temperature of the reaction mixture does not exceed 20° C., 96 g of (allyloxypropyl)methyldichlorosilane, which has been prepared in accordance with (a) above, and a solution of 11 g of trimethylchlorosilane in 100 g of toluene. After the reaction mixture has reacted for an additional one hour at room temperature, 300 ml of water are added to the reaction mixture and the reaction mixture is stirred until two clear phases have been formed. The aqueous phase is removed and the organic phase is freed from traces of acid using sodium bicarbonate solution. This solution is then dried by azeotropic distillation, and a diorganopolysiloxane blocked in the terminal positions with trimethylsiloxy groups and composed of dimethylsiloxane units and (allyloxypropyl)methylsiloxane units having an average ratio of Si-bonded allyloxypropyl radicals to Si-bonded methyl radicals of 0.028 and a viscosity of about 100 mm$^2$.s at 25° C. is obtained by subsequent evaporation in vacuo at 5 hPa (abs.).

(c) About 200 ppm (based on the total weight of the diorganopolysiloxane) of tris(triphenylphosphine)ruthenium(II) dichloride are added to 50 g of the diorganopolysiloxane obtained in (b) above. After eight hours at 130° C., a diorganopolysiloxane having a viscosity of about 230 mm$^2$.s at 25° C. is obtained, in which the allyloxypropyl radicals have almost quantitatively been rearranged into 1-propenyloxypropyl radicals.

The ratio of trans-isomers to cis-isomers is 35:65. The following $^1$H—NMR spectrum is obtained:

| $^1$H-NMR spectrum (CDCl$_3$): | |
|---|---|
| trans-isomer: | δ = 4.7 ppm (1H, CH$_3$—C$\underline{H}$=), |
| | 6.1 ppm (1H, =CH—O—). |
| cis-isomer: | δ = 4.3 ppm (1H, CH$_3$—C$\underline{H}$=), |
| | 5.8 ppm (1H, =CH—O—). |

EXAMPLE 4

(a) Ethylene glycol bis(allyl ether) is obtained by reacting allyl chloride with ethylene glycol in an analogous procedure to that used in the preparation of diallyl ether in accordance with Example 1(a) above.

(b) About 1.5 ml of a solution of platinum tetrachloride in 1-octene, containing 60 mg of platinum, calculated as the element, are added to 142 g of ethylene glycol bis(allyl ether). The mixture is heated to 130° C., then 69 g of a dimethylpolysiloxane having dimethylhydrogensiloxy groups as terminal units and an average molecular weight of 690 g/mole are added dropwise. After conversion of more than 99 percent of all Si-bonded hydrogen atoms in the dimethylpolysiloxane, all components which are volatile at 100° C. and at 5 hPa (abs.) are removed by distillation. A clear dimethylpolysiloxane product is obtained, having terminal units of the formula CH$_2$=CHCH$_2$OCH$_2$CH$_2$O(CH$_2$)$_3$(CH$_3$)$_2$SiO$_{\frac{1}{2}}$ and an average ratio of Si-bonded allyloxyethyloxypropyl radicals to Si-bonded methyl radicals of 0.104, and a viscosity of 13.8 mm$^2$.s at 25° C.

(c) About 200 ppm (based on the total weight of dimethylpolysiloxane) of RuHCl(PPh$_3$)$_3$ are added to 50 g of the dimethylpolysiloxane obtained in (b) above. After heating for eight hours at 130° C., a dimethylpolysiloxane having a viscosity of 23.4 mm$^2$.s is obtained, whose allyloxyethyloxypropyl groups have almost completely (97 percent conversion according to the $^1$HNMR spectrum) been rearranged to form 1-propenyloxyethyloxypropyl groups. The ratio of trans-isomers to cis-isomers is 26:74.

| $^1$H—NMR spectrum (CDCl$_3$): | |
|---|---|
| trans-isomer: | δ = 4.79 ppm (dq, 1H, CH$_3$—C$\underline{H}$=), |
| | 6.26 ppm (dq, 1H, =CH—O—). |
| cis-isomer: | δ = 4.40 ppm (dq, 1H, CH$_3$—C$\underline{H}$=), |
| | 5.98 ppm (dq, 1H, =CH—O—). |

EXAMPLE 5

(a) Allyl but-2-enyl ether is obtained by reacting but-2-en-1-ol with allyl chloride in an analogous procedure to that used in the preparation of diallyl ether in accordance with Example 1(a) above.

(b) About 84 g of allyl but-2-enyl ether are heated under reflux (about 120° C.) in a three-necked flask fitted with a reflux condenser, stirrer and dropping funnel. To this are added dropwise over a period of two hours a solution containing 82 g of triethoxysilane, in which 2 mg of platinum, calculated as the element, are dissolved in the form of a solution of platinum tetrachloride in 1-octene. After heating for an additional five hours under reflux, more than 99 percent of the Si-bonded hydrogen atoms have been converted. The intermediate obtained in this manner, (but-2-enyloxypropyl)triethoxysilane, is purified by distillation at 104° C. and at 7 hPa (abs.) and contains 5 percent by weight, based on the total weight of the intermediate, of (but-1enyloxypropyl)triethoxysilane.

(c) About 200 ppm (based on the total weight of intermediate) of tris(triphenylphosphine)ruthenium(II) dichloride are added to 50 g of the intermediate obtained in (b) above. After heating for eight hours at 130° C., the (but-1-enyloxypropyl)triethoxysilane is obtained in a yield of 70 percent. The ratio of trans-isomers to cis-isomers is 35:65. The product gives the following $^1$H—NMR spectrum:

| $^1$H—NMR spectrum (CDCl$_3$): | |
|---|---|
| trans-isomer: | δ = 0.63 ppm (m, 2H, Si—CH$_2$—), |
| | 0.93 ppm (t, 3H, CH$_3$—CH$_2$—CH=), |
| | 1.19 ppm (t, 9H, Si—O—CH$_2$—CH$_3$), |
| | 1.70 ppm (m, 2H, Si—CH$_2$—CH$_2$—), |
| | 1.89 ppm (ddq, 2H, CH$_3$—CH$_2$—CH=) |
| | 3.55 ppm (t, 2H, —O—CH$_2$—CH$_2$—), |
| | 3.76 ppm (q, 6H, Si—O—CH$_2$—), |
| | 4.72 ppm (dt, 1H, CH$_3$—CH$_2$—CH=CH—), |
| | 6.14 ppm (dt, 1H, CH$_3$—CH$_2$—CH=CH—). |
| cis-isomer: | δ = 0.63 ppm (m, 2H, Si—CH$_2$—), |
| | 0.92 ppm (t, 3H, CH$_3$—CH$_2$—CH=), |
| | 1.19 ppm (t, 9H, Si—O—CH$_2$—CH$_3$), |
| | 1.70 ppm (m, 2H, Si—CH$_2$—CH$_2$—), |
| | 2.04 ppm (ddq, 2H, CH$_3$—CH$_2$—CH=) |
| | 3.63 ppm (t, 2H, —O—CH$_2$—CH$_2$—), |
| | 3.76 ppm (q, 6H, Si—O—CH$_2$—), |
| | 4.25 ppm (dt, 1H, CH$_3$—CH$_2$—CH=CH), |
| | 5.81 ppm (dt, 1H, CH$_3$—CH$_2$—CH=CH—). |

EXAMPLE 6

(a) About 240 g of a diorganopolysiloxane having terminal trimethylsiloxy groups and composed of methylhydrogensiloxane units and dimethylsiloxane units, having 0.08 percent by weight of Si-bonded hydrogen and an average chain length of 80, are heated under reflux with 120 g of diallyl ether and 0.2 g of a solution of platinum tetrachloride in 1-octene which contains 8 mg of platinum, calculated as the element, until the amount of Si-bonded hydrogen used has been reduced to 2 percent. The excess of diallyl ether is distilled off at 60° C. and at 5 hPa (abs.). The intermediate obtained is a diorganopolysiloxane having terminal trimethylsiloxy groups and is composed of methyl(allyloxypropyl)siloxane units and dimethylsiloxane units, and has a viscosity of 460 mm$^2$.s at 25° C.

(b) About 200 ppm (based on the total weight of intermediate) of RuHCl(PPh$_3$)$_3$ are added to 50 g of the intermediate obtained in (a) above. After heating for eight hours at 130° C., the product obtained is a diorganopolysiloxane having terminal trimethylsiloxy groups and composed of methyl(1-propenyloxypropyl)siloxane units and dimethylsiloxane units. The ratio of trans-isomers to cis-isomers is 34:66. The product gives the following $^1$H—NMR spectrum:

| $^1$H-NMR spectrum (CDCl$_3$): | |
|---|---|
| trans-isomer: | δ = 4.7 ppm (1H, CH$_3$—CH=), |
| | 6.2 ppm (1H, =CH—O—). |
| cis-isomer: | δ = 4.3 ppm (1H, CH$_3$—CH=), |
| | 5.9 ppm (1H, =CH—O—). |

EXAMPLE 7

About 2 g of a 50 percent solution of bis(dodecylphenyl)iodonium hexafluoroantimonate, which has been prepared according to U.S. Pat. No. 4,279,717 in propenylene carbonate are added to 50 g of the product prepared in Example 6. The mixture is applied with a doctor blade to a polyethylene film to a thickness of 100 μ. Two medium pressure mercury lamps with an output of 80 watt/cm of tube length are arranged at a distance of 10 cm from the coated polyethylene film. After exposure to UV light for two seconds, a tack-free coating is obtained.

What is claimed is:

1. An organopolysiloxane having at least one Si-bonded Y$^1$ radical per molecule of the formula $$-(CH_2)_2-R^2-(A-R^3)_z-O-CH_2-CH=CH-R^4 \quad (II).$$

in which A is selected from the group consisting of of —O—, —S— and

—C—O,

R$^2$ is selected from the group consisting of an alkylene radical having from 1 to 7 carbon atoms(s) per radical and a cycloalkylene radical having from 5 to 7 carbon atoms per radical, R$^3$ is selected from the group consisting of an alkylene radical having from 2 to 4 carbon atoms per radical and an alkylene radical having from 2 to 4 carbon atoms per radical which is substituted with a group selected from the group consisting of a hydroxyl group, methoxy group, ethoxy group and a trimethylsiloxy group, R$^4$ is selected from the group consisting of a hydrogen atom and an alkyl radical having from 1 to 4 carbon atom(s) per radical and z is 0, 1 or 2.

2. The organopolysiloxane of claim 1, wherein the organopolysiloxane has units of the general formula $$R_a(R^1O)_bY_c^1SiO_{\frac{4-(a+b+c)}{2}}$$

in which R is selected from the group consisting of a monovalent unsubstituted hydrocarbon radical and a monovalent substituted hydrocarbon radical having from 1 to 18 carbon atom(s) per radial, R$^1$ is selected from the group consisting of a monovalent hydrocarbon radical having from 1 to 8 carbon atom(s) per radical and a monovalent hydrocarbon radical having from 1 to 8 carbon atom(s) per radical, which is interrupted by an ether oxygen atom, and Y$^1$ is a radical of the formula $$-(CH_2)_2-R^2-(A-R^3)_z-O-CH_2-CH=CH-R^4 \quad (II)$$

in which A, R$^2$, R$^3$, R$^4$ and z are as defined in claim 1, a is 0, 1, 2 or 3, b is 0, 1, 2 or 3, and c is 0 or 1, and the sum of a+b+c is ≦4.

3. An organopolysiloxane having at least one Si-bonded Y$^1$ radical per molecule of the formula $$-(CH_2)_2-R^2-(A-R^3)_z-O-CH_2-CH=CH-R^4 \quad (II).$$

in which A is selected from the group consisting of —O—, —S— and $$-\overset{\overset{\displaystyle O}{\|}}{C}-O,$$

$R^2$ is selected from the group consisting of an alkylene radical having from 1 to 7 carbon atom(s) per radial and a cycloalkylene radical having from 5 to 7 carbon atoms per radical, $R^3$ is selected from the group consisting of an alkylene radical having from 2 to 4 carbon atoms per radical and an alkylene radical having from 2 to 4 carbon atoms per radical which is substituted with a group selected from the group consisting of a hydroxyl group, methoxy group, ethoxy group and a trimethylsiloxy group, $R^4$ is selected from the group consisting of a hydrogen atom and an alkyl radical having from 1 to 4 carbon atoms(s) per radical and z is 0, 1 or 2, said organopolysiloxane is obtained by reacting an organic compound (1) of the formula $$H_2C=CH=R^2-(A-R^3)_z-O-CH_2-CH= CH-R^4$$

in which A, $R^2$, $R^3$, $R^4$ and z are as defined above, with an organpolysiloxane (2b) having at least one Si-bonded hydrogen atom in its molecule in the presence of a catalyst (3) which promotes the addition of Si-bonded hydrogen to the aliphatic double bond.

4. The organopolysiloxane of claim 3, wherein the organopolysiloxane (2b) has at least one Si-bonded hydrogen atom and is represented by the formula $$H_cR_{3-c}SiO(SiR_2O)_o(SiRHO)_pSiR_{3-c}H_c.$$

in which R is selected from the group consisting of a monovalent unsubstituted hydrocarbon radical and a monovalent substituted hydrocarbon radical having from 1 to 18 carbon atom(s) per radical, c is 0 or 1, o is 0 or an integer of from 1 to 1000, and p is 0 or an integer of from 1 to 500.

5. The organopolysiloxane of claim 3, wherein the organic compound (1) of the formula $$H_2C=CH-R^2-(A-R^3)_z-O-CH_2CH=CH-R^4$$

in which A, $R^2$, $R^3$, $R^4$ and z are as defined in claim 3, is reacted with a silane (2a) having an Si-bonded hydrogen atom of the formula $$R_dHSiX_{3-d}.$$

in which R is selected from the group consisting of a monovalent unsubstituted hydrocarbon radical and a monovalent substituted hydrocarbon radical having from 1 to 18 carbon atom(s) per radical, X is selected from the group consisting of a halogen atom and a radical of the formula $-OR^1$, in which $R^1$ is selected from the group consisting of a monovalent hydrocarbon radical having from 1 to 8 carbon atom(s) per radical and a monovalent hydrocarbon radical having from 1 to 8 carbon atoms(s) per radical which is interrupted by an ether oxygen atom and d is 0, 1 or 2, in the presence of a catalyst (3) which promotes the addition of Si-bonded hydrogen to the aliphatic double bond. to form a silane having an Si-bonded $Y^1$ radical of the formula $$-(CH_2)_2-R^2-(A-R^3)_z-O-CH_2-CH= CH-R^4 \qquad (II).$$

in which A, $R^2$, $R^3$, $R^4$, and z are the same as above. converting the silane having an Si-bonded $Y^1$ radical to an organopolysiloxane by reacting the silane with chlorosilanes or alkoxysilanes and/or condensable organopolysiloxanes to form an organopolysiloxane having at least one Si-bonded $Y^1$ radical of the formula $$-(CH_2)_2-R^2-(A-R^3)_z-O-CH_2-CH= CH-R^4 \qquad (II).$$

in which A, $R^2$, $R^3$, $R^4$, and z are the same as above.

6. The organopolysiloxane of claim 1, in which A is $-O-$ and z is 1 or 2.

7. The organopolysiloxane of claim 1, in which A is $$-\overset{\overset{\displaystyle O}{\|}}{C}-O$$

and z is 1 or 2.

8. An organosilane having at least one Si-bonded $Y^1$ radical per molecule of the formula $$-(CH_2)_2-R^2-(A-R^3)_z-O-CH_2-CH= CH-R^4 \qquad (II).$$

in which A is selected from the group consisting of $-O-$, $-S-$ and $$-\overset{\overset{\displaystyle O}{\|}}{C}-O,$$

$R^2$ is selected from the group consisting of an alkylene radical having from 1 to 7 carbon atoms(s) per radical and a cycloalkylene radical having from 5 to 7 carbon atoms per radical, $R^3$ is selected from the group consisting of an alkylene radical having from 2 to 4 carbon atoms per radical and an alkylene radical having from 2 to 4 carbon atoms per radical which is substituted with a group selected from the group consisting of a hydroxyl group, methoxy group, ethoxy group and a trimethylsiloxy group, $R^4$ is selected from the group consisting of a hydrogen atom and an alkyl radical having from 1 to 4 carbon atom(s) per radical and z is 1 or 2.

* * * * *

UNITED STATES PATENT AND TRADEMARK OFFICE
CERTIFICATE OF CORRECTION

PATENT NO.  : 5,118,772
DATED       : June 2, 1992
INVENTOR(S) : Christian Herzig and Doris Gilch It is certified that error appears in the above-identified patent and that said Letters Patent is hereby corrected as shown below:

On the title page, item (30) delete "Apr. 5, 1989" and insert
--- May 5, 1989 ---.

Column 15, line 20, delete "$H_2C=CH=R^2-(A-R^3)_z-O-CH_2-CH=CH-R^4$" and insert
--- $H_2C=CH-R^2-(A-R^3)_z-O-CH_2-CH=CH-R^4$ ---.

Signed and Sealed this

Twenty-fourth Day of August, 1993

Attest:

BRUCE LEHMAN

*Attesting Officer*   *Commissioner of Patents and Trademarks*